US00PP10945P

United States Patent [19]

Fuess

[11] Patent Number: Plant 10,945

[45] Date of Patent: Jun. 8, 1999

[54] CHRYSANTHEMUM PLANT NAMED 'EMPIRE SUNSHINE'

[76] Inventor: Janet S. Fuess, 22 Country Club Dr., New York Mills, N.Y. 13417

[21] Appl. No.: 08/990,232

[22] Filed: Dec. 15, 1997

[51] Int. Cl.[6] ..... A01H 5/00

[52] U.S. Cl. ..... Plt./82.2

[58] Field of Search ..... Plt./82.2

[56] References Cited

U.S. PATENT DOCUMENTS

P.P. 9,094 3/1995 Fuess ..... Plt./82.2

*Primary Examiner*—Howard J. Locker
*Attorney, Agent, or Firm*—C. A. Whealy

[57] ABSTRACT

A distinct cultivar of Chrysanthemum plant named 'Empire Sunshine', characterized by its uniformly mounded plant habit; daisy-type inflorescences that are about 6 cm in diameter; bright yellow ray florets; numerous inflorescences per plant; and excellent garden performance.

1 Drawing Sheet

The present invention relates to a new and distinct cultivar of Chrysanthemum plant, botanically known as *Dendranthema grandiflora* and referred to by the cultivar name 'Empire Sunshine'.

The new cultivar is a product of a planned breeding program conducted by the inventor in New York Mills, N.Y. The objective of the breeding program is to create new garden-type Chrysanthemum cultivars having inflorescences with desirable inflorescence forms and floret colors and good garden performance.

The new cultivar originated from a cross made by the inventor in October, 1992, of the *Dendranthema grandiflora* cultivar 'Empire Citrine' (U.S. Plant Pat. No. 9,094) as the female, or seed, parent with an unidentified proprietary seedling selection as the male, or pollen, parent, described as a yellow daisy-type garden Chrysanthemum.

The cultivar 'Empire Sunshine' was discovered and selected by the inventor as a flowering plant within the progeny of the stated cross in a controlled environment in New York Mills, N.Y, in September, 1993. The selection of this plant was based on its desirable inflorescence form and floret colors and excellent garden performance.

Asexual reproduction of the new cultivar by terminal cuttings taken in a controlled environment in New York Mills, N.Y, has shown that the unique features of this new Chrysanthemum are stable and reproduced true to type in successive generations.

The cultivar 'Empire Sunshine' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Empire Sunshine'. These characteristics in combination distinguish 'Empire Sunshine' as a new and distinct cultivar:

1. Uniformly mounded plant habit.
2. Daisy-type inflorescences that are about 6 cm in diameter.
3. Attractive bright yellow ray florets.
4. Numerous inflorescences per plant.
5. Excellent garden performance.

The new Chrysanthemum is similar in ray floret color and form to the Chrysanthemum culitvar 'Donna' (disclosed in U.S. Plant Pat. No. 7,512). However in side-by-side comparisons in Leamington, Ontario, Canada, under commercial practice, plants of the new Chrysanthemum differed from plants of the cultivar 'Donna' in the following characteristics:

1. Plants of the new Chrysanthemum are taller than plants of the cultivar 'Donna'.
2. The lower leaf lobes of plants of the new Chrysanthemum are longer than the lower leaf lobes of plants of the cultivar 'Donna'.
3. Plants of the new Chrysanthemum flower later than plants of the cultivar 'Donna'.
4. Plants of the new Chrysanthemum have smaller inflorescences than plants of the cultivar 'Donna'.
5. Plants of the new Chrysanthemum have three to five rows of ray florets whereas plants of the cultivar 'Donna' have a single row of ray florets.
6. Plants of the new Chrysanthemum have shorter corolla tubes than plants of the cultivar 'Donna'.
7. Ray florets of plants of the new Chrysanthemum have dentate apices whereas ray florets of plants of the Chrysanthemum cultivar 'Donna' have pointed apices.
8. Ray florets of plants of the new Chrysanthemum are darker in color than ray florets of plants of the cultivar 'Donna'.

BRIEF DESCRIPTION OF THE PHOTOGRAPHS

The accompanying photographs illustrate the overall appearance of the new cultivar.

The photograph at the top of the sheet comprises a side perspective view of a typical flowering plant of 'Empire Sunshine'.

The photograph at the bottom of the sheet comprises a close-up view of typical inflorescences of the cultivar 'Empire Sunshine'.

These photographs show the colors as true as it is reasonably possibe to obtain in colored reproductions of this type. Floret and foliage colors in the photographs may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., under conditions which approximate those generally used in commercial garden Chrysanthemum production. One unrooted cutting was directly stuck in a 15-cm container and plants were grown in a greenhouse with night interruption lighting for two weeks during late May/early June. At the end of the night interruption lighting period, plants were pinched (terminal apices removed). Three days later, plants were moved into an outdoor production area. Plants flowered about eight weeks later. Measurements and numerical values represent averages for typical flowering containers.

Botanical classification: *Dendranthema grandiflora* cultivar 'Empire Sunshine'.

Commercial classification: Daisy-type garden Chrysanthemum.

Parentage:

*Female or seed parent.*—*Dendranthema grandiflora* cultivar 'Empire Citrine', disclosed in U.S. Plant Pat. No. 9,904 .

*Male or pollen parent.*—Unidentified proprietary seedling selection described as a yellow daisy-type garden Chrysanthemum.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Perennial herbaceous daisy-type garden Chrysanthemum. Inverted triangle. Stems initially upright, then spreading giving a uniformly mounded appearance to the plant. Freely branching; about seven lateral branches develop after removal of terminal apex (pinching). Numerous secondary lateral branches develop at every node.

*Plant height.*—About 25 cm.

*Foliage description.*—Leaf arrangement: Alternate. Length: About 6.5 cm. Width: About 6.5 cm. Apex: Mucronate. Base: Attenuate. Margin: Palmately lobed, sinuses parallel. Texture: Upper and lower surfaces slightly pubescent. Veins prominent on lower surface. Petiole length: About 2 cm. Color: Young foliage upper surface: 147A. Young foliage lower surface: Lighter than 147A. Mature foliage upper surface: 147A. Mature foliage lower surface: Lighter than 147A. Venation upper surface: 147A or slightly lighter. Venation lower surface: 147B.

Inflorescence description:

*Appearance.*—Daisy-type inflorescence form. Inflorescences borne on terminals above foliage, arising from leaf axils. Disk and ray florets arranged acropetally on a capitulum. One inflorescence per terminal with numerous inflorescences per plant.

*Flowering response.*—Under natural conditions, plants flower in the autumn. Plants exposed to 1.5 to 2 weeks of long day/short night conditions after planting followed by short day/long night conditions flower about 59 days later.

*Inflorescence size.*—Diameter: About 6 cm. Depth (height): About 1 cm. Diameter of disc: About 1.3 cm.

*Ray florets.*—Shape: Oblong, flat to curved upward. Length: About 3 cm. Width: About 8 mm. Apex: Tri-dentate to rounded. Margin: Entire. Texture: Smooth, glabrous. Orientation: Slightly upright to horizontal, positioned about 90 to 110° to the peduncle. Number of ray florets per inflorescence: About 75, three to five rows. Color: When opening: 9A/7A. Opened inflorescence: Upper surface: 9A/7A. Lower surface: 9B/7B to 7D.

*Disc florets.*—Shape: Enlarged tubular, apex dentate. Length: About 7mm. Width: Apex: About 1.75 mm. Base: About 1 mm. Number of disc florets per inflorescence: Numerous. Color: Immature: 154A. Mature: Apex: 13A. Mid-section: Light green. Base: White.

*Peduncle.*—Aspect: Flexible, angled about 30° to the stem. Length: First peduncle: About 5 cm. Fourth peduncle: About 7 cm. Texture: Pubescent. Color: Lighter than 147A.

*Reproductive organs.*—Androecium: Present on disc florets only. Anther color: 13A/14A. Pollen: Amount: Moderate. Color: 17A. Gynoecium: Present on both ray and disc florets.

Disease resistance: No known Chrysanthemum diseases observed to date on plants grown under commercial production conditions.

Seed production: Seed production has not been observed.

It is claimed:

1. A new and distinct cultivar of Chrysanthemum plant named 'Empire Sunshine', as illustrated and described.

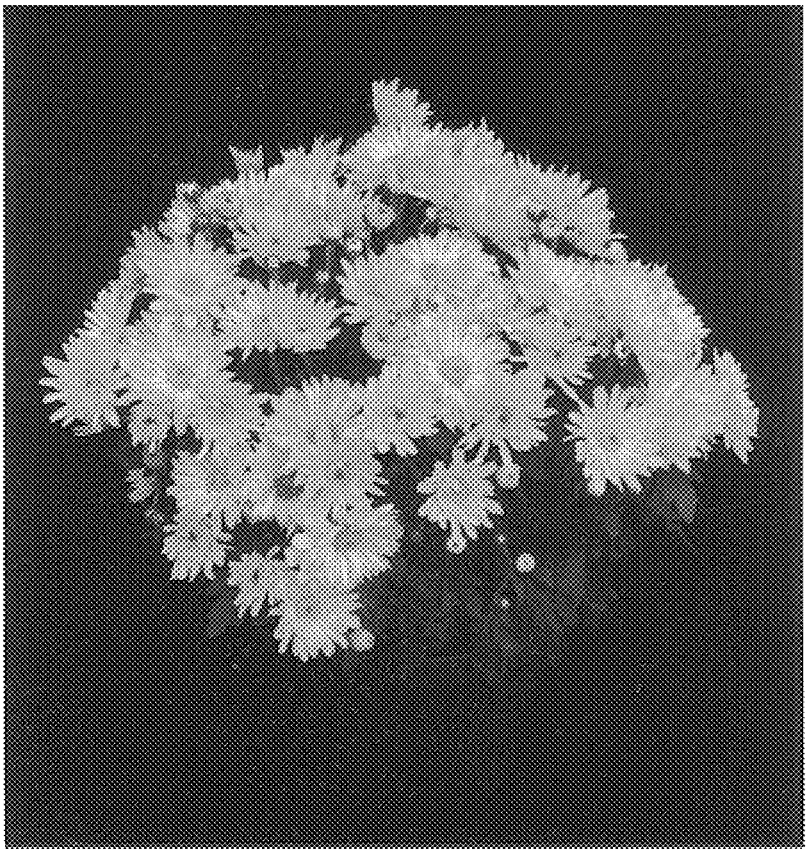
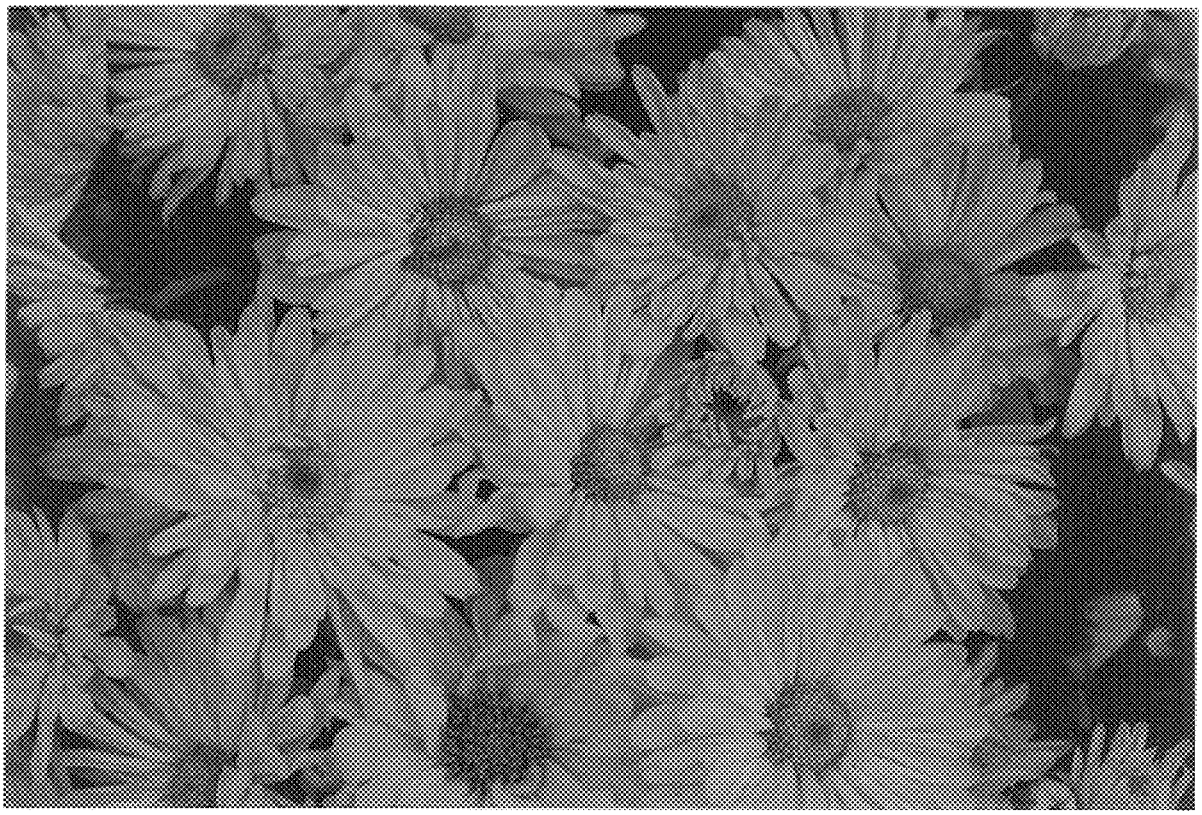

* * * * *